United States Patent [19]

Rasberger et al.

[11] 4,208,525

[45] Jun. 17, 1980

[54] REDUCTION OF 4-OXO-TETRAALKYLPIPERIDINES

[75] Inventors: Michael Rasberger, Riehen; Peter Baumeister, Basel, both of Switzerland

[73] Assignee: Ciba-Geigy Corporation, Ardsley, N.Y.

[21] Appl. No.: 857,485

[22] Filed: Dec. 5, 1977

[30] Foreign Application Priority Data

Dec. 9, 1976 [CH] Switzerland .................. 15500/76

[51] Int. Cl.$^2$ .................. C07D 211/12; C07D 211/14
[52] U.S. Cl. .................................................. 546/184
[58] Field of Search .................... 260/293.52; 546/184

[56] References Cited

PUBLICATIONS

Krö, E., I. G. Farbenindustrie, A.G., Publication 63165, 4/22/40.
Theilheimer, W., *Synthetic Methods of Organic Chemistry*, Interscience, New York, vol. 16 (1962), p. 51, vol. 17 (1963), p. 28.
Barnes, R., et al., *J. Am. Chem. Soc.*, 80, 4714–4716 (1958).
Mailey, E., et al., *J. Org. Chem.*, 22, 1061–1065 (1957).
Fankhauser, R., et al., Helv. Chim. Acta, 49, 690–695 (1966).
Fieser, L., et al., *Organic Chemistry*, Reinhold Pub. Co., New York, 1960, pp. 206, 231 and 544.
Augustine, R., *Catalytic Hydrogenation*, Marcel Dekker, New York, 1965, pp. 82–83, 90–91 and 106 (1965).
House, H. O., *Modern Synthetic Reactions*, W. A. Benjamin, New York, 1965, pp. 2 and 6–7.

*Primary Examiner*—Henry R. Jiles
*Assistant Examiner*—Richard A. Schwartz
*Attorney, Agent, or Firm*—Vincent J. Cavalieri; Luther A. R. Hall

[57] ABSTRACT

Process for the reduction of 4-oxo-2,2,6,6-tetraalkylpiperidines, and the N-alkyl derivatives thereof, to 2,2,6,6-tetraalkylpiperidines unsubstituted in the 4-position, wherein the reduction is carried out with catalytically activated hydrogen in an acid medium.

8 Claims, No Drawings

REDUCTION OF 4-OXO-TETRAALKYLPIPERIDINES

The invention relates to a process for the reduction of 4-oxo-2,2,6,6-tetraalkylpiperidines, and the N-alkyl derivatives thereof, to corresponding piperidines unsubstituted in the 4-position.

2,2,6,6-Tetrasubstituted piperidines unsubstituted in the 4-position, and the derivatives thereof, such as derivatives substituted on the N atom, are valuable stabilisers for plastics, such as polyolefines, in order to protect these against decomposition by light or heat, as is described, for example, in German Offenlegungsschrift No. 2,418,540 and German Offenlegungsschrift No. 2,621,841.

These tetraalkylpiperidines unsubstituted in the 4-position are generally obtained from the corresponding 4-oxopiperidines by reduction with hydrazine (compare the above German Offenlegungsschriften and also Bikova et al., C.A. Vol 56, 10088d (1956); Simon et al., C.A. Vol. 60, 8698 (1963) and Simon et al., C.A. Vol. 62, 9098h (1965)), whilst the 4-oxopiperidines, in turn, are accessible from ammonia and a ketone, such as acetone, or their condensation products, compare, for example, German Offenlegungsschrift No. 2,429,936 or German Offenlegungsschrift No. 2,429,937.

However, this previously known process for the reduction of 4-oxotetraalkylpiperidines is not very suitable for commercial application. The results of this reduction are not commensurate with the expense incurred.

It was, however, also known that 2,2,6,6-tetramethyl-4-oxopiperidine (triacetonamine) can be reduced to the corresponding 4-OH compound, in particular by catalytic means, such as with hydrogen and platinum in ethanol (Mailey et al., J.Org. Chem. 22 (1957) 1061–1065) or Raney nickel in ethanol (Zhelyazkov, Farmatsiya (Sofia) 13 (3), 11–17 (1963) and Frankhauser et al., Helvetica Chim. Acta 49 (1966) 690–695). It was the more surprising to find that a particular embodiment of this catalytic reduction leads, in good yields, to very pure piperidines unsubstituted in the 4-position.

The invention accordingly relates to a process for the reduction of 4-oxo-2,2,6,6-tetraalkylpiperidines, and the N-alkyl derivatives thereof, to 2,2,6,6-tetraalkylpiperidines unsubstituted in the 4-position, characterised in that the reduction is carried out with catalytically activated hydrogen in an acid medium.

The reduction can be carried out in a manner which is in itself known for catalytic hydrogenations.

Suitable catalysts are, in particular, transition metals and transition metal oxides of the 8th sub-group of the periodic table of the elements, as such or on a support, such as active charcoal, kieselguhr, aluminium oxide, barium sulphate or the like. Rh, Ru, Pd and, in particular, Pt are preferred. The hydrogenation is preferably carried out under a hydrogen pressure of 1–350 bars and especially of 1–5 bars, and at 0°–150° C., and especially at 0°–100° C.

Preferably, the 4-oxo-2,2,6,6-tetraalkylpiperidines are used in the form of their hydrates but the anhydrous bases can also be employed. The 4-oxopiperidines are preferably of high purity and are used, in particular, in concentrations of about 10–50% by weight.

Suitable solvents are alcohols, such as alkanols, especially those with 1–6 C atoms, such as methanol or ethanol, and also cyclic ethers, such as dioxane or tetrahydrofurane, as well as methylcellosolve, diglymes, dimethylformamide, esters, such as ethyl acetate, glacial acetic acid and hydrocarbons. Water, methanol, ethanol, tetrahydrofurane, dioxane, ethyl acetate and glacial acetic acid, as well as mixtures of such solvents, are preferred.

An inorganic acid, such as a mineral acid, especially perchloric acid, hydrochloric acid, phosphoric acid and particularly sulphuric acid, or an organic acid with a corresponding $pk_A$-value, is used as the acid added. The acid is used in amounts such as 1–8 equivalents of acid, relative to the piperidine, especially 1–4 equivalents of acid.

The process according to the invention offers a new, technically simple means of access 2,2,6,6-tetraalkylpiperidines unsubstituted in the 4-position, in high yield and high purity. The catalysts preferably used can with regard to educt be used in a small amount and can advantageously be recycled with only a small loss of activity. The high selectivity of the reduction prevents the formation of undesired by-products. Isolation of the piperidines unsubstituted in the 4-position in thus greatly simplified.

It was not foreseeable that the process according to the invention would offer these advantages. Neither was it foreseeable that a catalytic reduction would be possible at all, nor that the reduction under such mild conditions would lead with such high selectivity to the 2,2,6,6-tetraalkylpiperidines unsubstituted in the 4-position, which are obtainable in this way.

The process according to the invention is particularly suitable for reducing 2,2,6,6-tetrasubstituted 4-oxopiperidines of the triacetonamine type, which are used as stabilisers or as starting materials for stabilisers. In the 2- and 6-positions, these compounds carry alkyl radicals, above all n-alkyl radicals, such as those with 1–8, and especially 1–4, C atoms, above all ethyl and very particularly methyl, such as, in particular, triacetonamine itself. However, the two substituents in the 2- and 6-positions can also be linked, such as 2,2- or 6,6-alkylene, for example tetramethylene or pentamethylene.

The invention is explained in the illustrative examples which follows.

EXAMPLE 1

10 g of triacetonamine hydrate are hydrogenated in 100 ml of deionised water, in the presence of chemically pure sulphuric acid (2 mols per mol of triacetonamine), with 1 g of platinum dioxide hydrate under a hydrogen pressure of 4 bars and at room temperature in a Parr hydrogenation apparatus until the absorption of hydrogen has ceased. The theoretically calculated amount of hydrogen is taken up during hydrogenation.

The catalyst is separated off from the hydrogenation solution by filtration. The hydrogenation solution is rendered alkaline with sodium hydroxide and the 2,2,6,6-tetramethylpiperidine is extracted with ether. The organic phase is dried over sodium sulphate and filtered and the ether is evaporated off. The residue is subjected to vacuum distillation. This gives 7.3 g of 2,2,6,6-tetramethylpiperidine (TMP) with a boiling point of 90°–91°/105 mm Hg. The yield is 89.6% of theory.

EXAMPLE 2

17.3 g of triacetonamine hydrate are hydrogenated in 170 ml of deionised water, in the presence of chemically pure sulphuric acid (2 mols per mol of triacetonamine), with 0.5 g of platinum dioxide hydrate under a hydrogen pressure of 3 bars and at a temperature of 50° C. until the absorption of hydrogen has ceased. Further processing is carried out according to Example 1 and yields 2,2,6,6-tetramethylpiperidine in practically quantitative yield.

EXAMPLES 3–9

Further Examples were carried out in a manner analogous to that of Example 2. The test conditions applied and the results obtained are summarised in the Table given below (TAA=triacetonamine).

| Example No. | Educt TAA × $H_2O$ (g) | Catalyst $PtO_2$ × $H_2O$ (g) | Solvent (ml) | Acid (M/MTAA) | $H_2$-Pressure (bars) | Temp. (°C.) | Yield TMP = Product of Example 1 |
|---|---|---|---|---|---|---|---|
| 3 | 17,3 | 0,5 | $H_2O$ (170) | $H_2SO_4$ (2) | 3 | 25 | quant. |
| 4 | 17,3 | 1,7 | $H_2O$ (170) | $H_2SO_4$ (4) | 3 | 25 | quant. |
| 5 | 17,3 | 1,7 | $H_2O$ (170) | $H_3PO_4$ (2) | 3 | 25 | quant. |
| 6 | 17,3 | 1,7 | $H_2O$ (170) | $H_2SO_4$ (2) | 0,1 | 25 | quant. |
| 7 | 10 | 1 | $H_2O$ (50) | HCl (8,6) | 4 | 25 | 90% |
| 8 | 10 | 1 | glacial acetic acid(100) | $H_2SO_4$ (2) | 4 | 25 | 80% |
| 9 | 10 | 1 | glacial acetic acid(100) | $HClO_4$ (2) | 4 | 25 | quant. |

EXAMPLE 10

15.5 g of triacetonamine (free base) are hydrogenated in 80 ml of methanol, in the presence of methanolic hydrochloric acid (4 mols per mol of triacetonamine), with 2 g of platinum dioxide hydrate under a hydrogen pressure of 3 bars and at room temperature until the absorption of hydrogen has ceased. Futher processing according to Example 1 yields the desired product TMP in practically quantitative yield.

EXAMPLE 11

17.3 g of triacetonamine hydrate are hydrogenated in 170 ml of deionised water, in the presence of chemically pure sulphuric acid (4 mols per mol of triacetonamine), with 5% platinum on a barium sulphate carrier under a hydrogen pressure of 3 bars and at a temperature of 50° C. until the absorption of hydrogen has ceased. Further processing according to Example 1 yields the desired product TMP in 80% yield.

EXAMPLE 12

20.0 g of N-methyl-2,2,6,6-tetramethylpiperidone-(4) are hydrogenated in 200 ml of deionised water, in the presence of chemically pure sulphuric acid (4 mols per mol of piperidone), with 3 g of platinum dioxide hydrate under a hydrogen pressure of 3 bars and at room temperature until the absorption of hydrogen has ceased. Further processing is carried out analogously to that for TMP according to Example 1 to yield N-methyl-2,2,6,6-tetramethylpiperidine in quantitative yield (b.p./17=70°–72° C.).

What is claimed is:

1. Process for the reduction of 4-oxo-2,2,6,6-tetraalkylpiperidine, or an N-alkyl derivative thereof, to 2,2,6,6-tetraalkylpiperidine or an N-alkyl derivative theory, respectively, unsubstituted in the 4-position, wherein the reduction is carried out with catalytically activated hydrogen in an acid medium.
2. Process according to claim 1, wherein the reduction is carried out with Pt, Pd, Rh or Ru and hydrogen.
3. Process according to claim 1, wherein the hydrogenation is carried out under 1–350 bars and at 0°–150° C.
4. Process according to claim 1, wherein a solvent and an acid are used as the acid medium.
5. Process according to claim 4, wherein the solvent used is water, methanol, ethanol, tetrahydrofurane, dioxane, ethyl acetate or glacial acetic acid.
6. Process according to claim 4, wherein the acid used is an inorganic acid.
7. Process according to claim 1, wherein the hydrogenation is carried out in water with sulphuric acid.
8. Process according to claim 1, wherein triacetonamine is reduced to 2,2,6,6-tetramethylpiperidine.